United States Patent [19]

Inage et al.

[11] Patent Number: 5,316,006

[45] Date of Patent: May 31, 1994

[54] ELECTRONIC BLOOD PRESSURE METER

[75] Inventors: Katuyuki Inage, Osaka; Yumi Saito, Kyoto; Zhang Zhimming, Osaka; Toru Fujii, Kyoto; Osamu Shirasaki, Hyogo, all of Japan

[73] Assignee: Omron Corporation, Kyoto, Japan

[21] Appl. No.: 27,537

[22] Filed: Mar. 8, 1993

[30] Foreign Application Priority Data

Mar. 9, 1992 [JP] Japan ................... 4-050105

[51] Int. Cl.⁵ ............................................. A61B 5/022
[52] U.S. Cl. ................................. 128/681; 128/680; 128/687
[58] Field of Search .............. 128/672, 677, 680–686, 128/687, 688–690

[56] References Cited

U.S. PATENT DOCUMENTS

| | | | |
|---|---|---|---|
| 3,814,083 | 6/1974 | Fletcher et al. | |
| 4,312,359 | 1/1982 | Olson | 128/680 |
| 4,461,266 | 7/1984 | Hood, Jr. et al. | 128/680 X |
| 4,534,361 | 8/1985 | Berger et al. | 128/680 |
| 4,800,892 | 1/1989 | Perry et al. | 128/677 |
| 4,850,368 | 7/1989 | Miyawaki | 128/680 |
| 4,928,701 | 5/1990 | Harada et al. | 128/677 |
| 5,165,416 | 11/1992 | Shinoda et al. | 128/687 X |
| 5,172,696 | 12/1992 | Souma | 128/687 X |

FOREIGN PATENT DOCUMENTS

| | | |
|---|---|---|
| 0029166 | 5/1981 | European Pat. Off. |
| 0332701 | 9/1989 | European Pat. Off. |
| 3143372 | 5/1983 | Fed. Rep. of Germany |

*Primary Examiner*—Angela D. Sykes
*Attorney, Agent, or Firm*—Fish & Richardson

[57] ABSTRACT

An electronic blood pressure meter including a cuff, a pressurizing means for inflating the cuff, a pressure sensing device for sensing a fluid pressure within the cuff, a pulse wave detecting device for detecting a pulse wave component included in the cuff, a systolic pressure estimating device for estimating a systolic pressure value based on the pulse wave and the cuff pressure detected in a pressurizing process, a pressurization volume computing device for computing a pressurization volume based on the estimated the systolic pressure value, a pressure decreasing device for decreasing the cuff pressure after reaching the pressurization volume, a blood vessel information detecting device for detecting blood vessel information such as pulse wave components in the pressure decreasing process, a blood pressure value determining device for determining systolic and diastolic pressure values based on the blood vessel information and the cuff pressure, a pulse wave component dispersion degree detecting device for detecting a dispersion degree of the pulse wave components obtained in the pressure decreasing process, and a pressurization volume controlling device for controlling the pressurization volume by the pressurizing device.

3 Claims, 18 Drawing Sheets

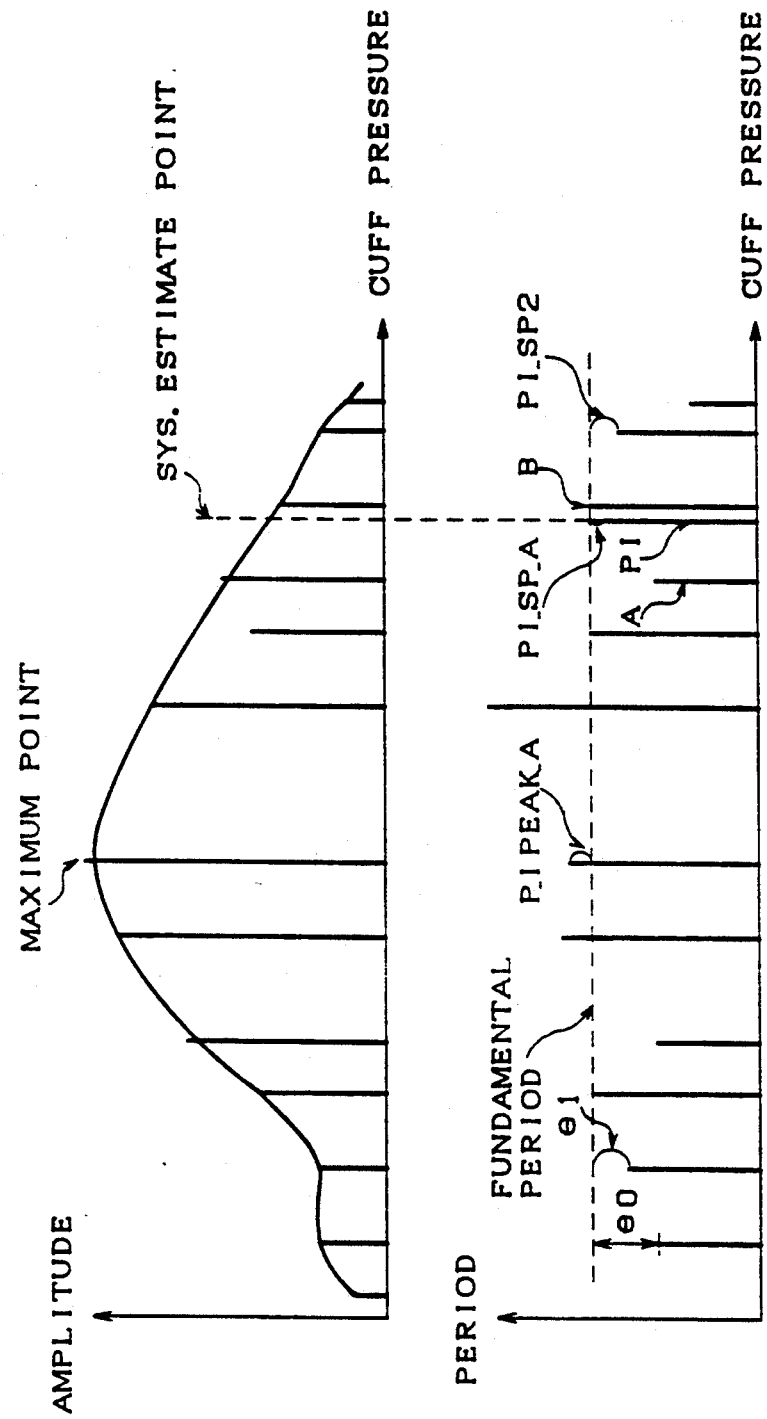

MF of PI_PEAK

MF of PI_SP

MF of PI_SP2

MF of PI_VAR

FIG. 10

| No. | IF (CONDITION) | | | | THEN (CONCLUSION) |
|---|---|---|---|---|---|
| | pivar | pipek | pisp | pisp2 | d1 |
| 1 | S | | | | H |
| 2 | B | B | | | L |
| 3 | M | B | | | L |
| 4 | B | S | B | | L |
| 5 | M | S | B | | L |
| 6 | B | S | M | B | M |
| 7 | M | S | M | B | M |
| 8 | B | S | S | B | M |
| 9 | M | S | S | B | M |
| 10 | B | S | S | M | H |
| 11 | M | S | S | M | H |
| 12 | B | S | S | S | H |
| 13 | M | S | S | S | H |
| 14 | M | S | M | M | H |
| 15 | M | S | M | S | H |
| 16 | B | S | M | M | M |
| 17 | B | S | M | S | M |

ELECTRONIC BLOOD PRESSURE METER

BACKGROUND OF THE INVENTION

Field of the Invention

This invention relates to an electronic blood pressure meter, and more particularly to an improved electronic blood pressure meter having a means for determining a pressurization volume to be applied to a cuff.

Discussion of the Related Art

An electronic blood pressure meter which inflates a cuff on pressure a portion of a body gradually decreases the cuff pressure after the cuff pressure a predetermined pressurization reference, detects a blood vessel sound (K sound) or a pulse wave component, and determines a systolic pressure and a diastolic pressure in view of the vessel sound and cuff pressure or the pulse wave component and cuff pressure is well known. The electronic blood pressure meter requires that the pressurization reference is greater than a systolic pressure point by a predetermined amount of pressure (hereinafter, called the pressurization margin) to ensure detection of the vessel sound or the pulse wave component in the cuff pressure decreasing process.

Accordingly, an electronic blood pressure meter which detects during pressure increasing process a vessel sound or a pulse on a cuff pressure in order to set a pressurization volume of a cuff by estimating a systolic pressure.

The electronic blood pressure meter, which estimates a systolic pressure value by a cuff pressure and a pulse wave amplitude in a pressurization process and which determines a pressurization volume based on the estimated systolic pressure value, invites large errors due to unusual amplitudes caused by period variations in which the pulse period is suddenly long or short as in an irregular pulse patient where the pulse amplitude becomes large in a long pulse period and small in a short pulse period and a pressurizing speed must be designed to be relatively fast for shortening a measuring time resulting in few obtainable pulse wave data. The pressurization volume computed according to such estimated value cannot achieve proper pressurization, and invites problems of insufficient pressure or over-pressure which require representation prolongation of measuring time, and unnecessary pressurization to persons to be measured.

SUMMARY OF THE INVENTION

It is, therefore, a primary object of this invention to provide an improved electronic blood pressure meter capable of setting a proper pressurization volume even in irregular pulse patients.

According to this invention, there is provided an electronic blood pressure meter including a cuff, a pressurizing means for inflating the cuff, a pressure sensing means for sensing a fluid pressure within the cuff, a pulse wave detecting means for detecting a pulse wave component included in the cuff, a systolic pressure estimating means for estimating a systolic pressure value based on the pulse wave and the cuff pressure detected in a pressurizing process, a pressurization volume computing means for computing a pressurization volume based on the estimated the systolic pressure value, a pressure decreasing means for decreasing the cuff pressure after reaching the pressurization volume, a blood vessel information detecting means for detecting blood vessel information such as pulse wave components in the pressure decreasing process, a blood pressure value determining means for determining systolic and diastolic pressure values based on the blood vessel information and the cuff pressure, a pulse wave component dispersion degree detecting means for detecting a dispersion degree of the pulse wave components obtained in the pressure decreasing process, and a pressurization volume controlling means for controlling the pressurization volume by the pressurizing means.

The electronic blood pressure meter, in the case of an irregular pulse wave patient who suddenly has a pulse wave period dispersion or a pulse wave amplitude dispersion, detects a dispersion degree of the dispersion by the pulse wave component dispersion degree detecting means and sets a large pressurization margin by the pressurization volume controlling means to execute precise blood pressure measurement without repressurization or remeasurement. In the case of the person that rarely has irregular pulses, the pressurization margin is set to the necessary minimum so as to shorten measurement time without decreasing accuracy.

BRIEF DESCRIPTION OF THE DRAWINGS

Other objectives and advantages of this invention will be more readily apparent from the following detailed description provided in conjunction with the following figures, of which:

FIG. 7 is a graph showing characteristic quantities and pulse waves in the electronic blood pressure meter of the second embodiment;

FIG. 10 shows a fuzzy inference rules of the electronic blood pressure meter of FIG. 7;

DETAILED DESCRIPTION OF PREFERRED EMBODIMENTS OF THE INVENTION

Figure 1:
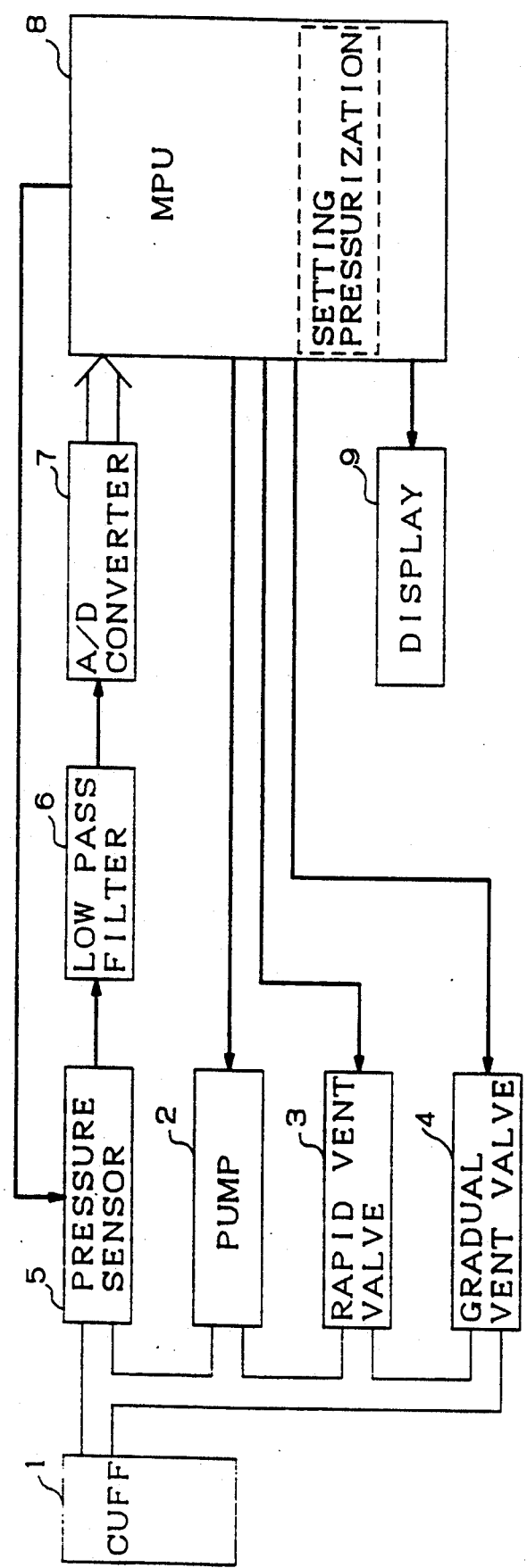
FIG. 1 is a schematic block diagram of an electronic blood pressure meter as a first embodiment of the invention.

FIG. 1, there is shown a schematic block diagram of an electronic blood pressure meter as a first embodiment of this invention. This invention is applied to an oscillation method type blood pressure meter and in particular to estimation of a systolic pressure in pressurizing a cuff.

The electronic blood pressure meter of FIG. 1 includes a cuff 1, a pump 2 for pressurization, a rapid vent valve 3, a gradual vent valve 4, a pressure sensor 5, a low pass filter 6, an A/D converter 7, a MPU (micro processor unit) 8, and a display 9. The pump 2 is designed to adjust a pressurization volume under control of MPU 8. An output from pressure sensor 5 is applied to A/D converter 7 through low pass filter 6 which is disposed to filter pressure noise generated from pump 2 pressurizing. A pressure signal converted to a digital signal by A/D converter 7 is applied to MPU 8. MPU 8 extracts the pressure signal from converter 7 and a pulse wave component superimposed on the pressure signal to operate a blood pressure determination described later. MPU 8 is designed to control a cuff pressure in the cuff 2 by controlling pump 2, rapid vent valve 3 and gradual vent valve 4, and applies a measured result to display 9 to be displayed. In the electronic blood pressure meter of this embodiment, the pressurization margin may be automatically set to four steps. The following operations will be done by a program stored in MPU 8 The following operations (2), (3), and (5) are characterized in this embodiment.

(1) Pulse wave extracting operation : A pulse wave is separated and extracted from a cuff signal by a filter (HPF).

(2) Pulse wave period computing operation : A pulse wave signal is detected in a pulse wave for each pulse to compute a pulse wave period.

(3) Pulse wave period dispersion computing operation : A dispersion of a pulse wave period computed by the above operation (2) is computed.

(4) Systolic pressure estimating operation in pressurization : A systolic pressure value is estimated by computing a pulse wave and a cuff pressure obtained in pressurizing.

(5) Pressurization volume setting operation : The best pressurization volume is computed by employing the dispersion of pulse wave periods computed in the operation (3) and the estimated systolic pressure values computed in the operation (4).

(6) Pressure measurement in decreasing pressure : Systolic and diastolic pressure is computed in view of pulse waves and cuff pressures obtained in decreasing cuff pressure.

Figure 2:
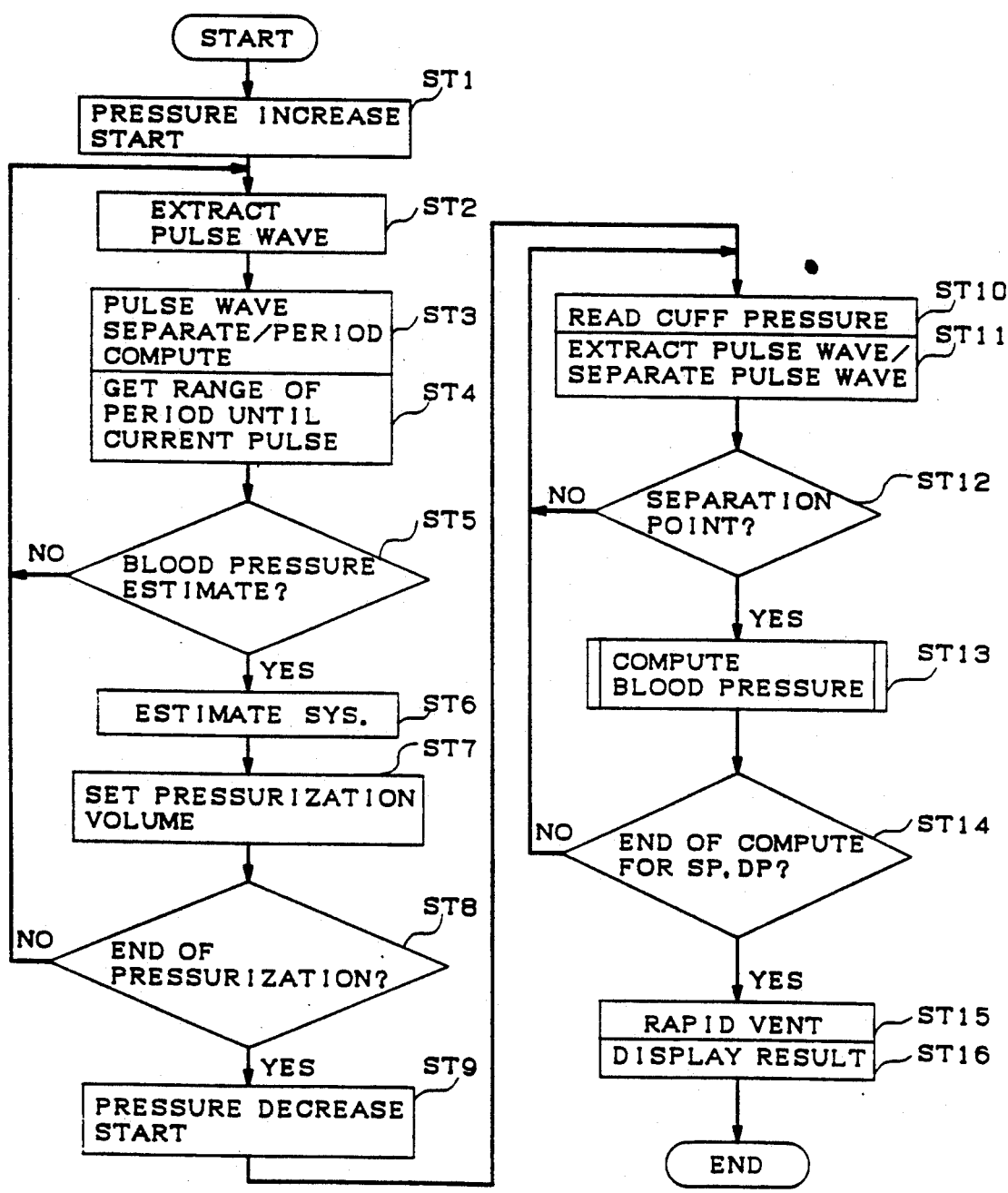
FIG. 2 is a flow chart illustrating a whole operation of the electronic blood pressure meter of FIG. 1.

In reference to the flow chart of FIG. 2, a complete sequence of the electronic blood pressure meter of this embodiment will be described hereinafter. Upon starting the operation by turning on a start switch, MPU 8 drives pump 2 to start pressure increase or pressurization in a step 1 (hereinafter, expressed as ST1). In ST2, a pulse wave component is extracted from cuff pressure data by a pulse wave extracting operation, which is a high pass filter realized by the above mentioned program. The pulse wave is separated, and if two or more pulses are detected in the pulse wave, the intervals or periods are computed to be stored in a storage for each pulse in ST3. In ST4 the periods stored in ST3 are read out to find the maximum and minimum values for a range width (maximum value–minimum value) of periods. In ST5 it is judged if estimation of a systolic pressure is available. If available, the sequence moves to ST6, and if not, it returns to ST2 to repeat the sequence from ST2 to ST5. In ST6, for instance, a pressurization corresponding to a half of the maximum value of the pulse wave amplitudes in a higher pressure side is estimated as a systolic pressure value, and the sequence moves to ST7.

In ST7 a pressurization volume or pressurization desired value is set by employing the range width computed in ST4 and the systolic pressure estimated value computed in ST6. This operation will be described in detail later.

In ST8 a current cuff pressure is compared with the pressurization desired value set in ST7. If it reaches the desired value, the sequence moves to ST9. Unless it reaches, the sequence returns to ST2 to repeat the sequence from ST2 and ST8. In ST9 MPU 8 stops the pressurization, and starts a gradual exhaust or pressure decrease.

An operation for blood pressure measurement is performed after start of the pressure decrease. In ST10 a cuff pressure signal is always read out, and in ST11 a pulse wave extracting operation similar to the operation in the pressurizing operation is executed. In ST12 it is inquired if a separating point of the pulse wave is detected. A Yes response from ST12 will be applied to ST 13, and a NO response will return to ST10 to repeat the sequence from ST10 to ST12.

If the sequence moves to ST13, a blood pressure measurement operation is executed. Its detailed explanation for blood pressure determination will be described later. In ST14 it is inquired if both systolic pressure SP and diastolic pressure DP have been computed. If both pressures have been computed, the sequence moves to ST15, but if not, it returns to ST10 to repeat the sequence from ST10 to ST14.

If SP and DP are found as a result of ST14, MPU 8 actuates fast vent valve 3 to exhaust pressure within cuff 1 (ST15), and a measurement result is displayed by display 9 (ST16) for completion of the whole operation.

Figure 3:
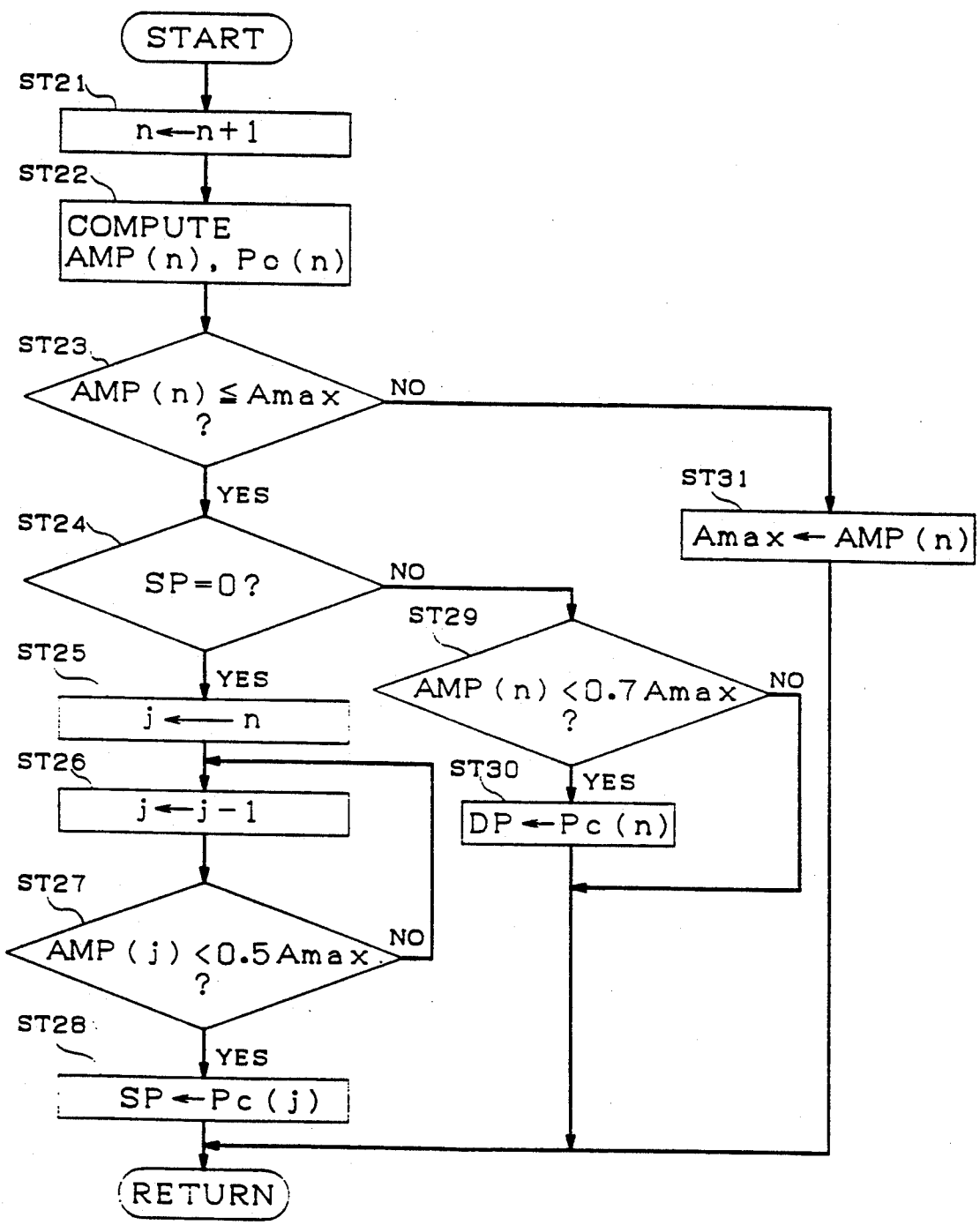
FIG. 3 is a flow chart for computing a blood pressure value in the operation of FIG. 2.

In view of a flow chart of FIG. 3, the operation of blood pressure computation in ST14 is explained in detail. Suppose that a separation point of pulse wave has been found in the pulse wave detection operation and that a pulse wave number n, systolic pressure SP and diastolic pressure DP are initialized to "0".

If a pulse wave number n is incremented by "1" (ST21), a pulse wave amplitude AMP(n) and its counterpart cuff pressure Pc(n) are computed (ST22). AMP(n) is compared with Amax (ST23). Amax is a variable presenting the largest value in the pulse wave amplitudes detected until the moment. If AMP(n-)>Amax, the sequence moves to ST31 supposing that an envelope of an pulse wave amplitude line does not reach the maximum point and Amax is substituted by the value of AMP(n) for return. If AMP(n)≦Amax in ST23, the envelop of pulse wave amplitude line is regarded that it has already passed the maximum point and is in a decreasing process, and the sequence moves to ST24 in which it is inquired if a variable SP of systolic pressure is "0". If SP=0, a SP computing operation consisting of steps from ST25 to ST28 is executed assuming that SP is not determined. If SP is already determined, the sequence moves to ST29.

In ST25 a counter j for a pulse wave is set to the current pulse wave number n, and in ST26 the counter j is decremented by "1" to compare the pulse wave amplitude AMP(j) designated by j with the maximum value Amax. If AMP(j)≦Amax×0.5 (ST27), the corresponding cuff pressure PC(j) is set to systolic pressure SP for return.

In ST29 and ST30 diastole pressure (diastolic pressure) computing operation is executed. In ST29 it is inquired if the pulse wave amplitude AMP(n) is decreased to DP computing threshold value (herein Amax×0.7 is defined) or smaller. If AMP(n-)≦Amax×0.7, the cuff pressure Pc(n) is set to a diastolic pressure DP for returning (ST30).

Figure 4:
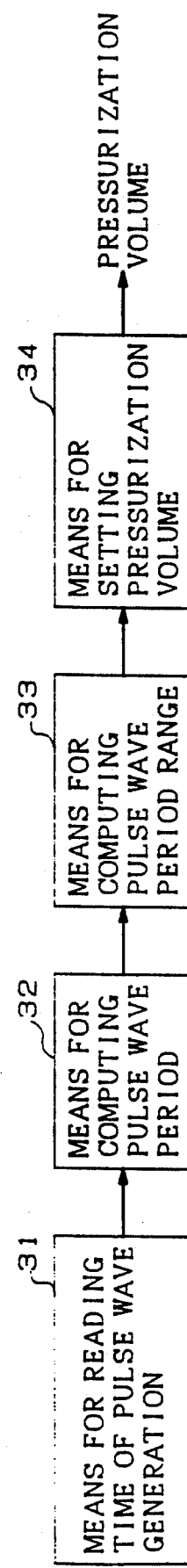
FIG. 4 is a schematic block diagram of a section of the electronic blood pressure meter for showing a function of setting a pressurization volume.

Next, the setting pressurization volume most characteristic in this embodiment will be explained. FIG. 4 shows a functional construction of the pressurization volume setting means which includes a means 31 for reading time of pulse wave generation from a data storage, a means 32 for computing pulse wave period, a means 33 for computing a pulse wave period range from the computed pulse wave periods, and a means 34 for setting a pressurization volume according to the computed pulse wave period range.

Figure 5:
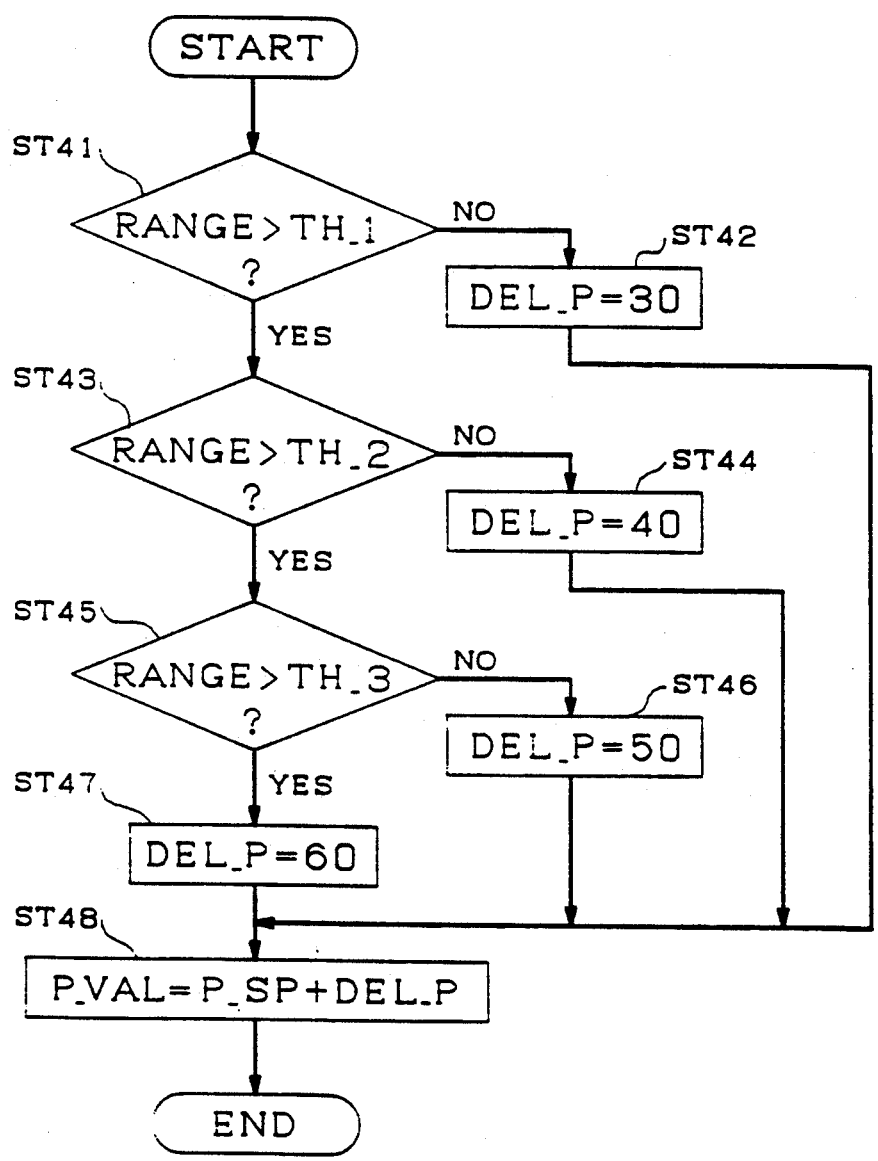
FIG. 5 is a flow chart showing a pressurization volume setting routine in the electronic blood pressure meter.

In view of a flow chart of FIG. 5, the pressurization volume setting operation in ST7 of FIG. 2 will be explained in detail. In the following description, RANGE is a range of period, DEL_P is a margin volume (in normal 30–40 mmHg is standard) to be added to an estimated value of systolic pressure, P_VAL is a pressurization volume (pressurization desired value), P_SP is a systolic pressure estimated value, TH_1, TH_2, and TH_3 are threshold values about a range of period.

Upon starting the pressurization volume setting routine, pulse wave period range RANGE is compared with threshold value TH_1 in ST41. If it is below the threshold value, a normal status is found and the pressurization margin DEL_P is set to standard volume 30 mmHg (ST42). If the period range RANGE is larger than threshold value TH_1 in ST41, it is compared with the next threshold value TH_2 (ST43). In the same manner as that of ST41, if RANGE is below the threshold value TH_2, it is regarded as relatively unusual status and the pressurization margin 40 mmHg a little higher than the margin in normal status is set (ST44). If the period range RANGE is larger than threshold value TH_2 in ST43, it is compared with threshold value TH_3 (ST43). If it is below value TH_3, a further higher pressurization margin 50 mmHg is set as unusual status.

If the period range RANGE is larger than the threshold value TH_3 in ST45, a still further high pressurization margin 60 mmHg is set (ST47). Thus, if setting of the pressurization margin DEL_P in steps ST41-ST47 is finished, the systolic pressure estimated value D_SP and the pressurization margin DEL_P are added to obtain the pressurization volume (pressurization desired value) P_VAL (ST48) for finishing the pressurization volume setting operation to be returned.

Next, a second embodiment of this invention will be described hereinafter. A schematic hardware construction of an electronic blood pressure meter is the same as that of FIG. 1. This second embodiment is characterized by pressurization volume computation employing fuzzy inference.

In the electronic blood pressure meter of this second embodiment, the following operations are executed by a program of MPU 8.

(1) Pulse wave extracting operation : the same as that of the first embodiment.
(2) Pulse wave period computing operation : the same as that of the first embodiment.
(3) Pulse wave period characteristic quantity computing operation : A characteristic quantity computed in the operation (2) is computed.
(4) Unusual degree computing operation : The characteristic quantity computed by the operation (3) is computed by fuzzy inference as an input thereof to generate a unusual degree.
(5) Systolic pressure estimating operation in pressurizing : A systolic pressure is computed from pulse wave data produced in pressurizing.
(6) Pressurization volume setting operation : A pressurization volume is computed by the unusual degree obtained in the operation (4) and the systolic pressure obtained in the operation (5).
(7) Blood pressure measurement in decreasing pressure : A systolic pressure is computed from wave obtained in decreasing pressure.

This embodiment is featured by the operations (2), (3), (4) and (6).

Figure 6:
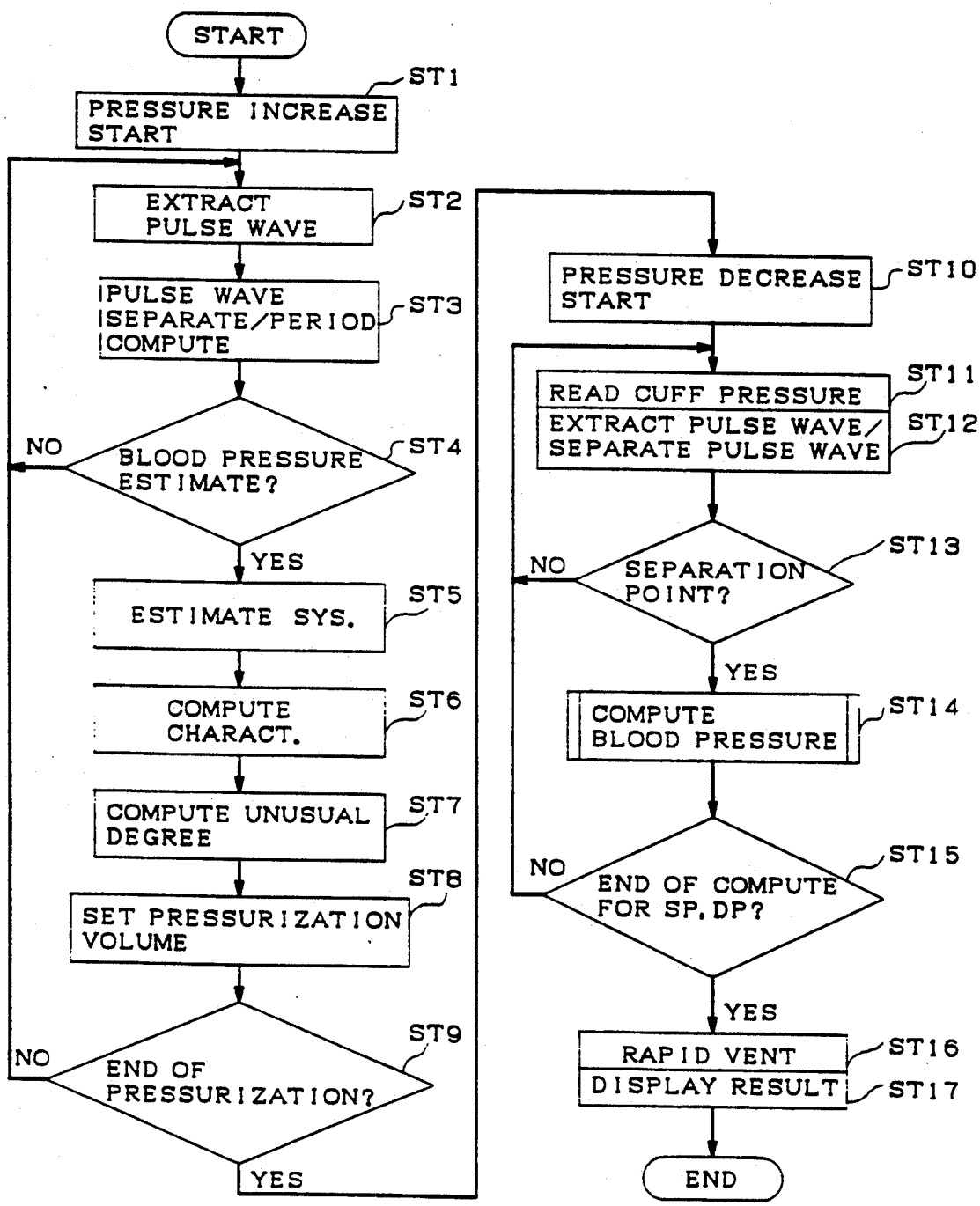
FIG. 6 is a flow chart illustrating a whole operation of an electronic blood pressure meter as a second embodiment of this invention.
Figure 8A:
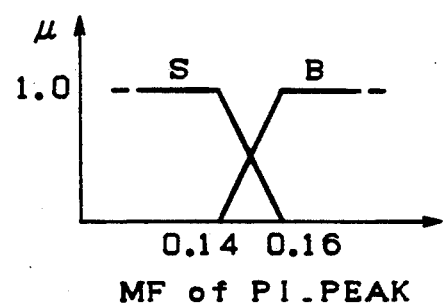
FIG. 8 shows membership functions at the antecedent of a fuzzy inference section of the electronic blood pressure meter of FIG. 7.
Figure 8B:
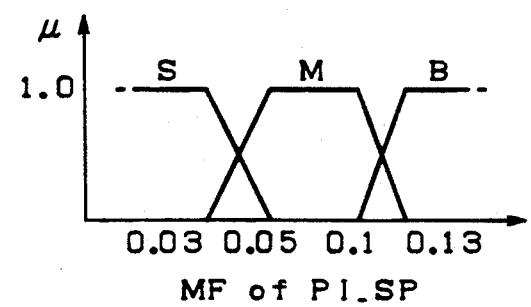
Figure 8C:
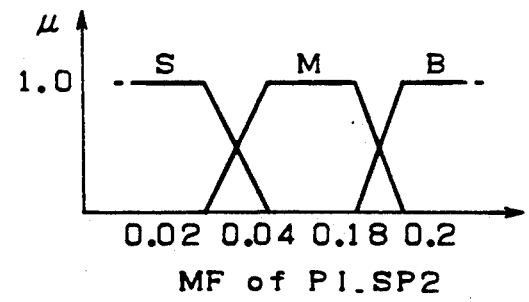
Figure 8D:
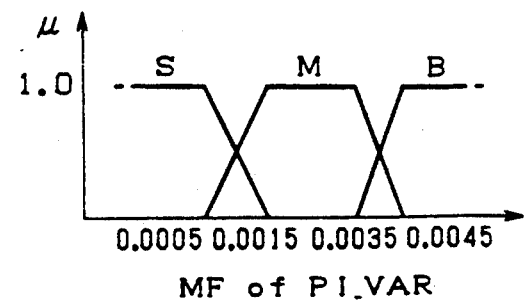

In reference to a flow chart of FIG. 6, a complete sequence of this embodiment will be described hereinafter. Upon starting the operation by turning a start switch, MPU 8 drives the pump to pressurize (ST1), and extracts a pulse wave component from cuff pressure data by a pulse wave extracting operation (ST2). If two or more pulses are detected in the pulse wave, an interval or period is computed to be stored in a storage for each pulse (ST3).

In ST4 it is inquired if estimation of a systolic pressure is possible. Unless possible, the sequence returns to ST2 to repeat the sequence from ST2 to ST3. The operation of ST4 and ST5 are the same as that of FIG. 2. In ST6 a characteristic quantity is computed based on a plurality of pulse wave periods stored until the moment, and in ST7 is employed to compute an unusual degree of a pulse wave amplitude in fuzzy inference, which will be explained later in detail.

Upon computing the unusual degree, a pressurization volume is set by employing the estimated systolic pressure value and unusual degree (ST8). In ST9 a current cuff pressure is compared with a computed pressurization desired value. If the cuff pressure reaches the desired value, the sequence moves to ST10 to start decreasing pressure supposing that the pressurization is finished. Unless reaches the value, the sequence returns to ST2 to repeat the sequence from ST2 to ST8. The sequence from ST10 to ST17 are the same as that of from ST9 to ST16.

The characteristic quantity is a dispersion of periodic deviation PI_VAR, a periodic deviation of maximum point PI_PEAK, a periodic deviation of systolic pressure estimating point PI_SP, a periodic deviation PI_SP2 of a pulse wave subsequent to pulse waves sandwiching the systolic pressure estimating point. In reference to FIG. 7, computation is executed about PI_VAR=ei/fundamental period, j (1 to number of periodic data), PI_PEAK=PI_PEAK_A/fundamental period, PI_SP=PI_SP_A (a period of systolic pressure point by proportional distribution of periods A and B), and PI_SP2=PI_SP2/fundamental period.

The computation of unusual degree in ST7 is performed by fuzzy inference accepting the above mentioned characteristic quantity computed from pulse wave periods as its input. According to the fuzzy inference of this embodiment, the inference method is MAX_MIN operation, the affirmative operation method is a weighted average in which the consequent membership function MF is singleton and the relevance degree of each rule is weight.

Figure 9:
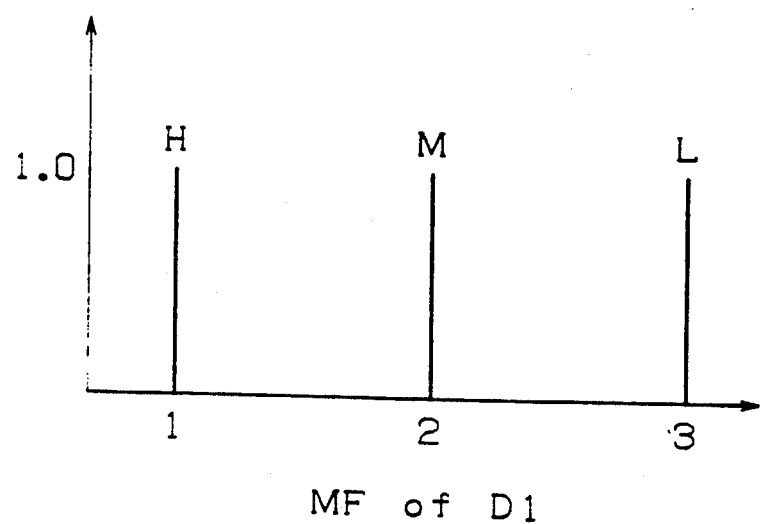
FIG. 9 shows membership functions at the consequent of the fuzzy inference section of the electronic blood pressure meter of FIG. 7.

FIG. 8 shows a membership function MF of antecedent, FIG. 9 shows a membership function of consequent, and FIG. 10 shows fuzzy inference rules. In the antecedent, S is small, M is middle, and B is big. In the consequent, H is a high unusual degree, M is a middle unusual degree, and L is a low unusual degree.

Figure 11:
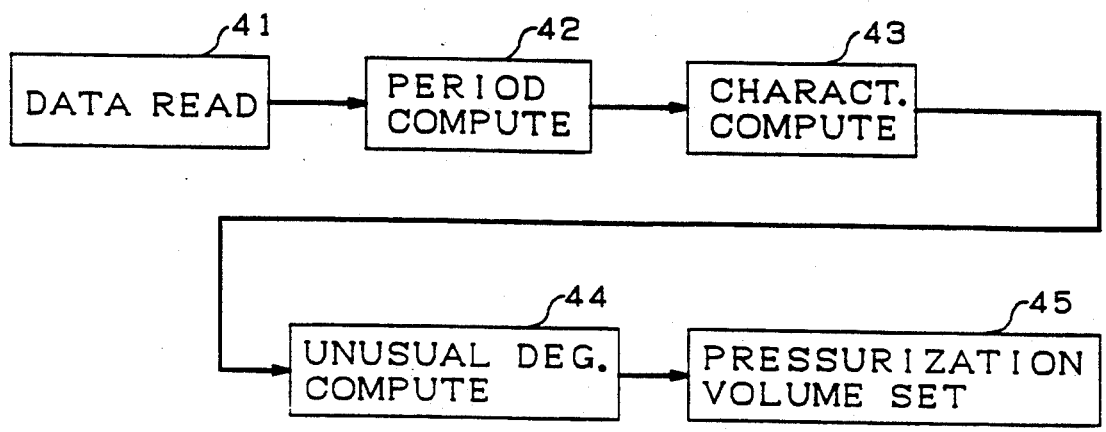
FIG. 11 is a schematic block diagram of a pressurization volume setting section of the electronic blood pressure meter of the second embodiment.

FIG. 11 shows a functional construction for setting a pressurization volume in FIG. 8, which includes a data read section 41 for reading a pulse wave generation time in data, a period compute section 42 for computing a time interval (period) of pulse wave generation based on the read time, a characteristic quantity compute section 43 for computing a characteristic quantity by employing periods, an unusual degree compute section 44 for computing a unusual degree of a pulse wave amplitude line from the characteristic quantity, and a pressurization volume set section 45 for determining a pressurization volume by employing the unusual degree and systolic pressure estimated value.

Figure 12:
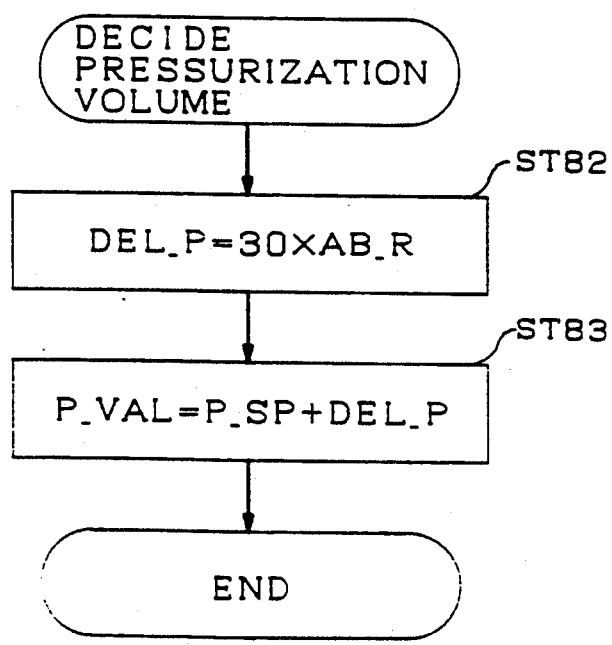
FIG. 12 is a flow chart illustrating an operation of the pressurization volume setting section of FIG. 11.

In FIG. 12, there is shown an actual flow chart for a pressurization volume determination operation. In ST82 a pressurization margin DEL_P is determined. The margin is normally 30–40 mmHg, but increased at a high unusual degree. In this embodiment 30 mmHg is set for normal state, and 90 mmHg is set for the worst of unusual degree. In ST83 the pressurization margin DEL_P is added to the systolic pressure estimated value P_SP to produce pressurization volume (pressurization desired value) P_VAL for finishing the operation.

An electronic blood pressure meter as a third embodiment of this invention will be described hereinafter. The hardware construction of the electronic blood pressure meter of this embodiment is the same as that of FIG. 1. This embodiment is featured by obtaining a dispersion degree (unusual degree) of a pulse wave based on the characteristic quantity of pulse wave amplitude in a pressurizing process to set a pressurization volume (pressurization desired value).

In the electronic blood pressure meter of this embodiment, the following operations are executed by a program of MPU 8.

(1) Pulse wave extracting operation : a filtering (HPF) operation for separating and extracting a pulse wave from a cuff pressure signal.

(2) Computing operation for a ratio of inclination of pulse wave amplitude and an average value of a pulse wave amplitude : a pulse wave is detected on the basis of a pulse wave signal for each pulse, a ratio of inclination of pulse wave amplitudes of backward and forward three pulses and an average value of the pulse wave amplitudes are computed, and the maximum value thereof is regarded as an average value of pulse wave amplitudes.

(3) Estimating operation of systolic pressure : An estimated value of systolic value is computed.

(4) Computing characteristic volume about maximum point and systolic pressure : ratio of inclination of amplitudes before and after maximum point, ratio of inclination of pulse wave amplitude just before systolic pressure, and ratio of inclination of pulse wave amplitude just after systolic pressure.

(5) Pressurization volume setting operation : Computing a pressurization volume in accordance with characteristic quantity of amplitudes of a pulse wave line.

(6) Computing operation of systolic and diastolic pressure values.

The operations (2), (4), and (5) are distinctive in this embodiment.

Figure 13:
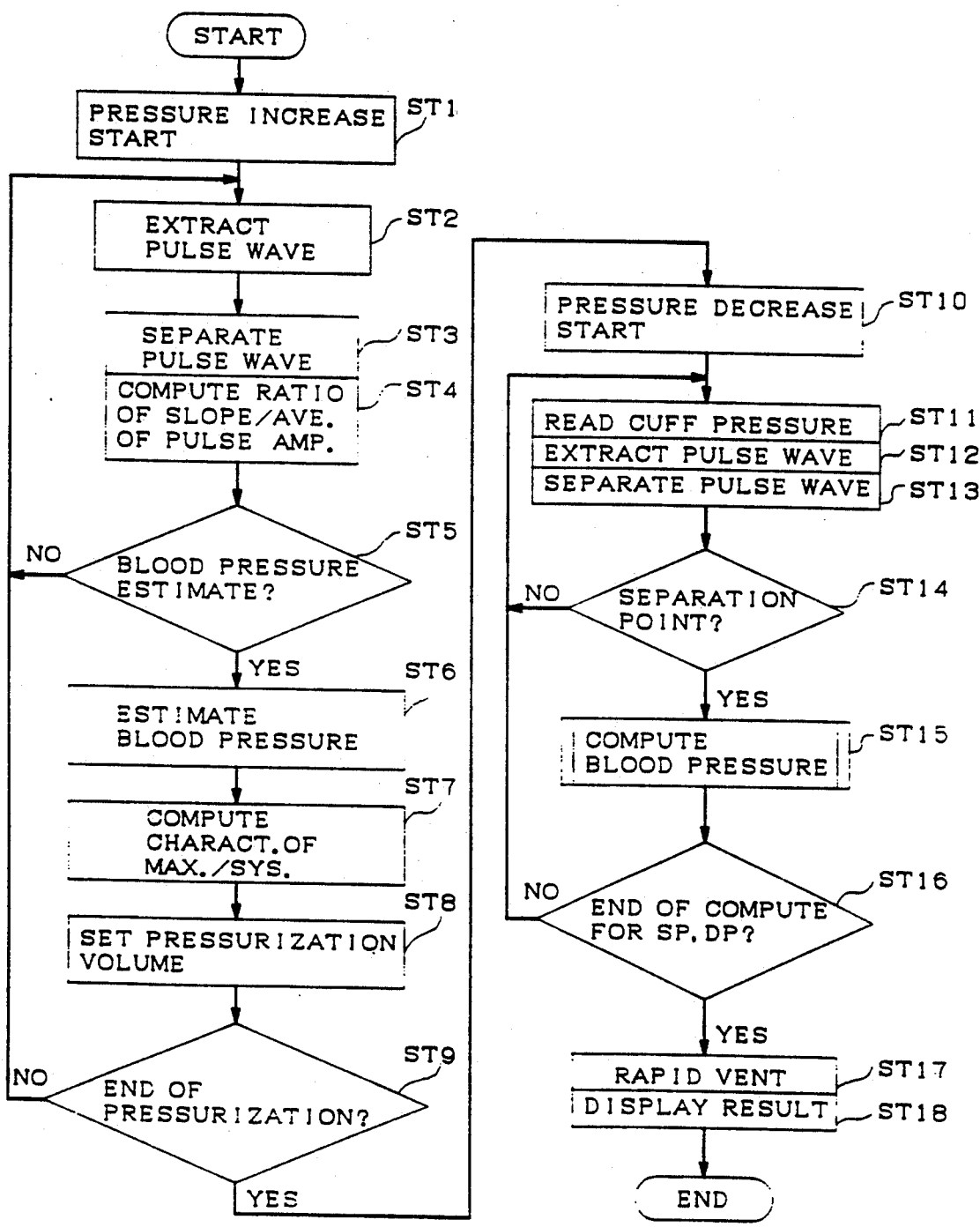
FIG. 13 is a flow chart illustrating a whole operation of an electronic blood pressure meter as a third embodiment of this invention.

In reference to a flow chart of FIG. 13, a complete sequence of the electronic blood pressure meter of this embodiment will be described.

Upon starting the operation by turning on a start switch, MPU 8 drives pump 2 to start pressurization (ST1).

In a pulse wave extracting operation (ST2), a pulse wave component is extracted from cuff pressure data. This presents a high pass filter performed by a program. If two or more pulses of pulse wave are detected, a ratio of the amplitudes and an average value of the amplitudes is computed and stored into a storage for each pulse (ST3 and ST4).

In ST5 it is inquired if a blood pressure estimation (systolic pressure) is possible. If possible, an estimating operation of systolic pressure is executed (ST6). Unless possible, the sequence returns to ST2 to repeat the sequence from ST2 to ST4.

Advancing to ST7, MPU 8 computes characteristic quantity relating to maximum point and systolic pressure stored until the moment, viz., a ratio of inclination of amplitudes before and after maximum point, ratio of inclination of amplitude just before systolic pressure, and ratio of inclination of amplitude just after systolic pressure.

Figure 16:
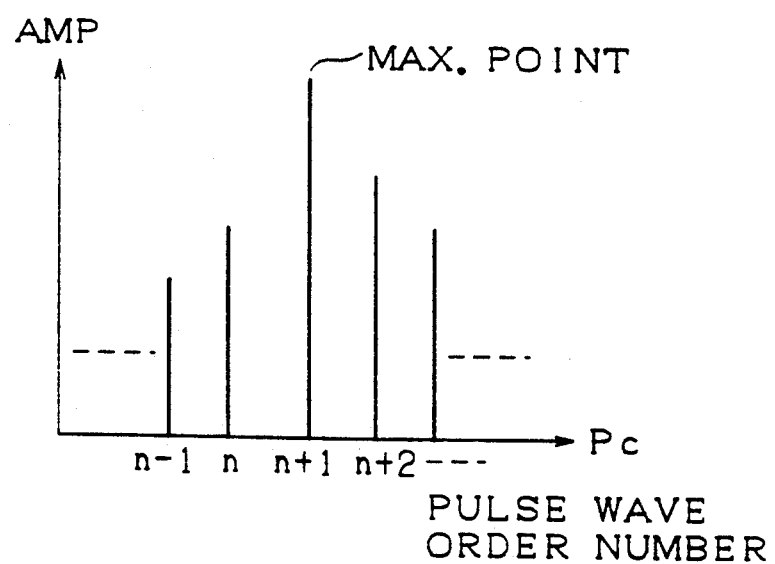
FIG. 16 is a graph illustrating a maximum point of a pulse wave amplitude.

As shown in FIG. 16, the maximum point of pulse wave amplitude corresponds to a maximum value in the pulse wave amplitudes arranged in the order of number which are extracted in a varying process of a cuff pressure. A ratio of inclination of amplitudes before and after a maximum point RATIO_PEAK is RATIO_PEAK = $\gamma/\delta$
is −10
when $\gamma$ = [AMP($n$ + 1) − AMP($n$)]/[Pc($n$ + 1) − Pc($n$)]
$\delta$ = [AMP($n$ + 1) − AMP($n$ + 2)]/[Pc($n$ + 2) − Pc($n$ + 1)]
$\delta$ = 0

Figure 17:
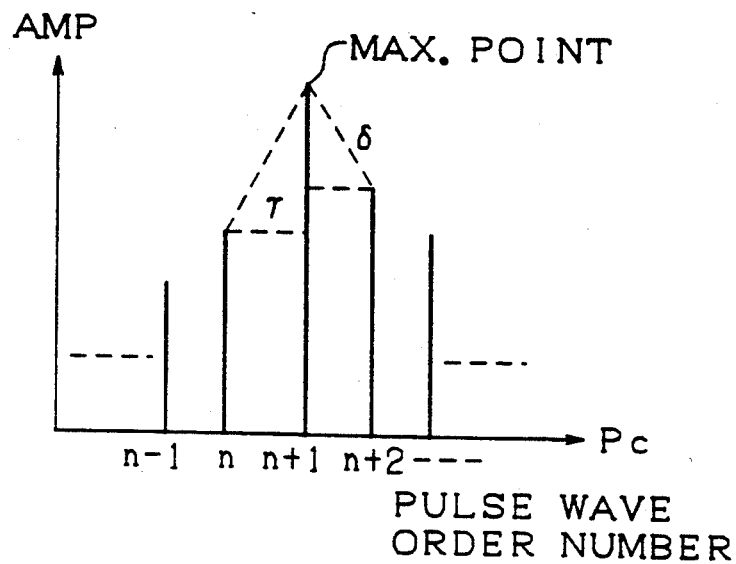
FIG. 17 is a graph illustrating computation of a ratio of inclinations of pulse wave amplitudes before and after a maximum point.

As shown in FIG. 17, $\gamma$ is a slope between the maximum point and an amplitude of a pulse just before the point, and $\delta$ is a slope between the maximum point and an amplitude of a pulse just after the point.

A ratio of inclination of pulse wave amplitude just before systolic pressure RATIO_SP_BF is expressed below.

RATIO_PEAK = $\eta/\theta$

Figure 18:
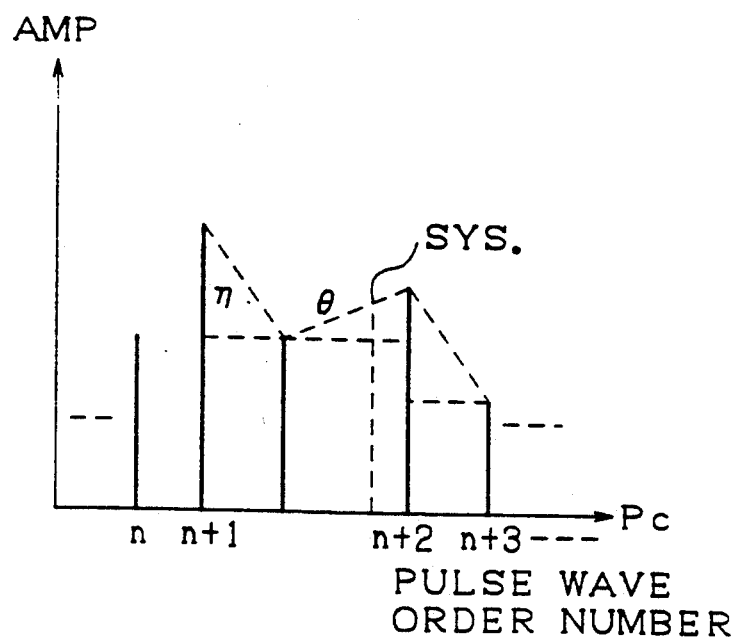
FIG. 18 is a graph illustrating a ratio of pulse wave amplitudes just before a systolic pressure.

-continued is $-10$
when $\eta = [AMP(n) - AMP(n + 1)]/[Pc(n) - Pc(n + 1)]$
$\theta = [AMP(n + 1) - AMP(n + 2)]/[Pc(n + 2) - Pc(n + 1)]$
$\theta = 0$ As shown in FIG. 18, $\eta$ is a slope between two pulse wave amplitudes before systolic pressure, and $\theta$ is a slope between amplitudes of a pulse before and a pulse after systolic pressure.

A ratio of inclination of pulse wave amplitude just after the systolic pressure RATIO_SP_AF is expressed below.

Figure 19:
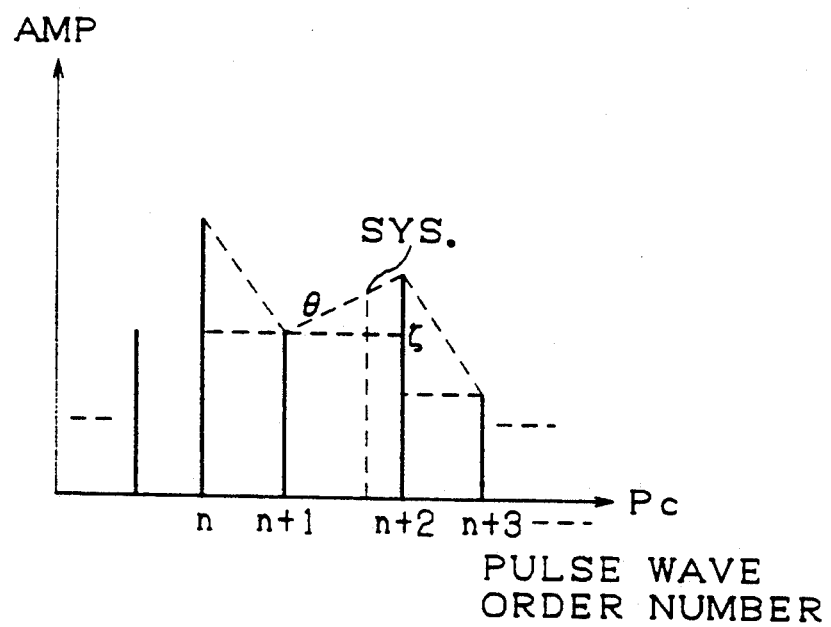
FIG. 19 is a graph illustrating a ratio of pulse wave amplitudes just after a systolic pressure.

RATIO_PEAK = $\theta/\zeta$
is $-10$
when
$\theta = [AMP(n + 1) - AMP(n + 2)]/[Pc(n + 1) - Pc(n + 2)]$
$\zeta = [AMP(n + 2) - AMP(n + 3)]/[Pc(n + 2) - Pc(n + 3)]$
$\zeta = 0$ As shown in FIG. 19, is a slope between pulse wave amplitudes of one pulse before and one pulse after systolic pressure, and is a slope between amplitudes of two pulse waves after systolic pressure.

In ST8 a proper pressurization volume is computed by a predetermined equation employing a plurality of characteristic quantity computed in ST4 and ST7.

In ST9 a pressurization volume (pressurization desired value) computed in ST8 and a cuff pressure at the corresponding time point are compared. If the cuff pressure reaches the desired value, the sequence moves to ST10, but unless reaches, it returns to ST2 to repeat the sequence ST2 to ST9.

In ST10 the MPU stops the pressurization, and starts a gradual exhaustion at a preset pressure decreasing speed by controlling vent valve 4. Since the operation after ST10 is the same as that of ST9 to ST16, its explanation is omitted.

Figure 15:
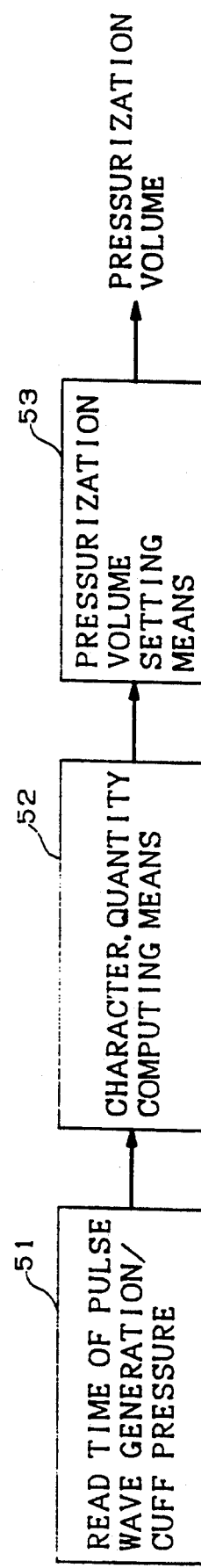
FIG. 15 is a schematic block diagram of a section of the electronic blood pressure meter of the third embodiment for setting a pressurization volume.

Next, computing characteristic quantity and setting pressurization volume important in this embodiment will be explained hereinafter. As shown in FIG. 15, a functional construction for setting a pressurization volume includes a means 51 for reading time of pulse wave generation and cuff pressure from a data storage, a means 52 for computing characteristic quantity from pulse wave amplitude data, and a means 53 for setting a pressurization volume from the computed characteristic quantity.

Figure 14:
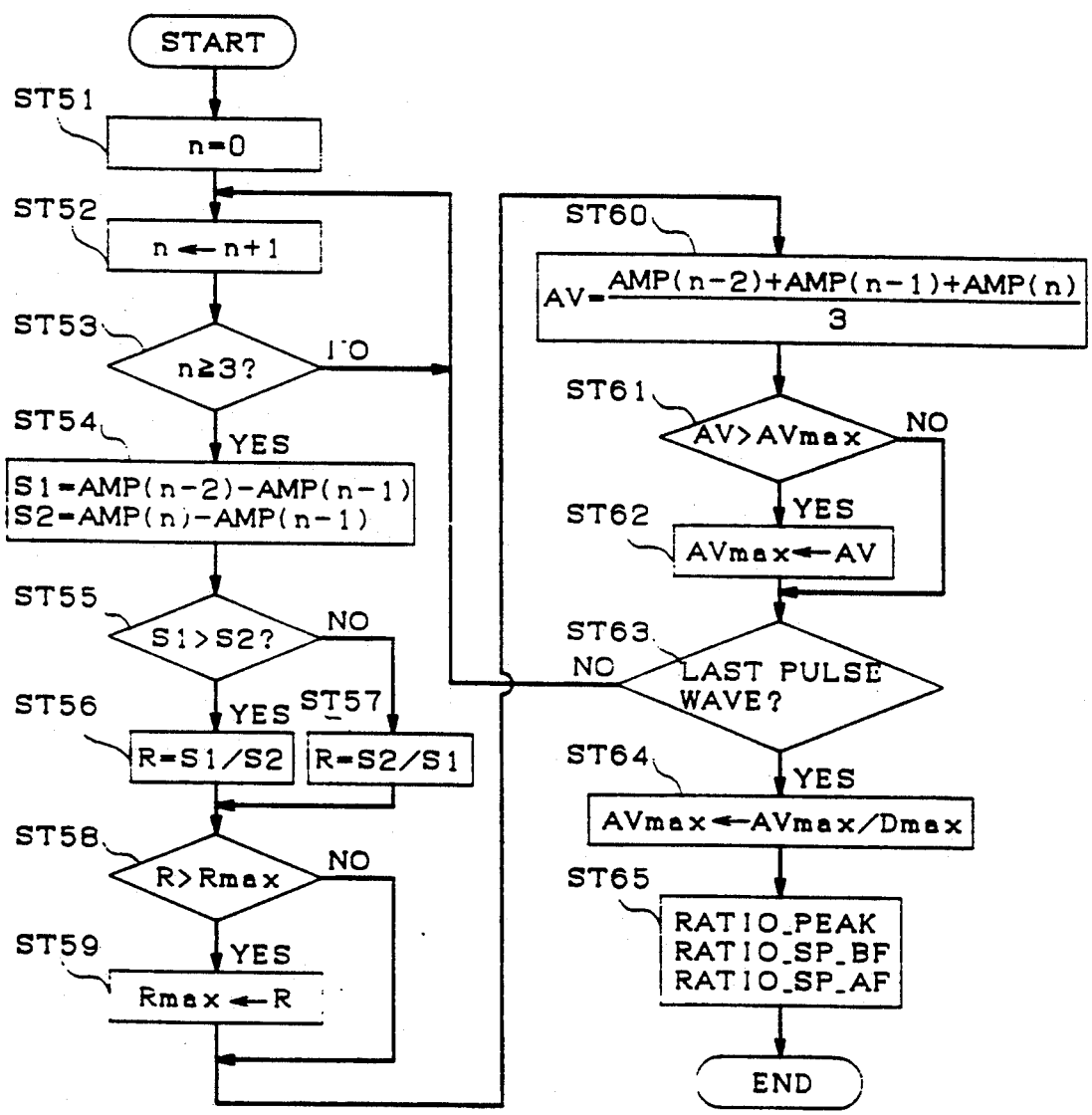
FIG. 14 is a flow chart illustrating an operation for computing a ratio of inclinations of pulse wave amplitudes and an average value of pulse wave amplitudes of backward and forward three pulses.

In reference to a flow chart of FIG. 14, a computing operation about characteristic quantity will be described. n is a pulse wave number, R is a ratio of inclination of pulse wave amplitude, Rmax is a maximum value of ratios of inclination of the maximum pulse wave amplitude, AV is an average value of pulse wave amplitudes of before-and-after three pulses, AVmax is an average value of pulse wave amplitudes of the maximum before-and-after three pulses in a pulse wave line, Dmax is the maximum pulse wave amplitude, RATIO_PEAK is a ratio of amplitudes before and after the maximum point, RATE10_SP_BF is a ratio of a pulse wave amplitude just before systolic pressure, and RATE10_SP_AF is a ratio of a pulse wave amplitude just after systolic pressure.

Upon resetting pulse wave number n (ST51), the pulse wave number n is incremented by "1" (ST52) and it is inquired if n is 3 or more (ST53). Unless 3 or more, the sequence returns to ST52 to increment n by "1". If n is 3 or more, the sequence moves to ST54 where a difference value S1 between the last but one pulse wave amplitude Amp(n−2) and the former pulse wave amplitude Amp(n−1) and a difference value S2 between a current pulse wave amplitude Amp(n) and the former pulse wave amplitude Amp(n−1) are computed for comparison of S1 and S2 (ST55). If S1 is larger than S2, R=S1/S2 is computed (ST56). If S1 is smaller than S2, R=S2/S1 is computed (ST57). In ST58 it is inquired if the ratio value R is larger than Rmax. If the ratio value R is larger than Rmax, the ratio value R is revised to Rmax (ST59). If the ratio value R is smaller than Rmax, the sequence jumps ST59 to ST60. In ST60 an average value AV of pulse amplitudes of three pulses of the current, former and the last but one pulses is computed. In ST61 it is inquired if the average value AV is larger than AVmax. If AV is larger than AVmax, AV is revised to AVmax (ST62). If AV is smaller than AVmax, the sequence jumps ST 62 to ST63. In ST63 it is inquired if it is the last pulse wave. The sequence ST60 to ST63 is repeated until the last pulse wave is found. When the last pulse wave is found, AVmax is revised by AVmax/Dmax as a new AVmax (ST64). In ST65 RATIO_PEAK, RATIO_SP_BF, and RATIO_SP_AF are computed.

Figure 20:
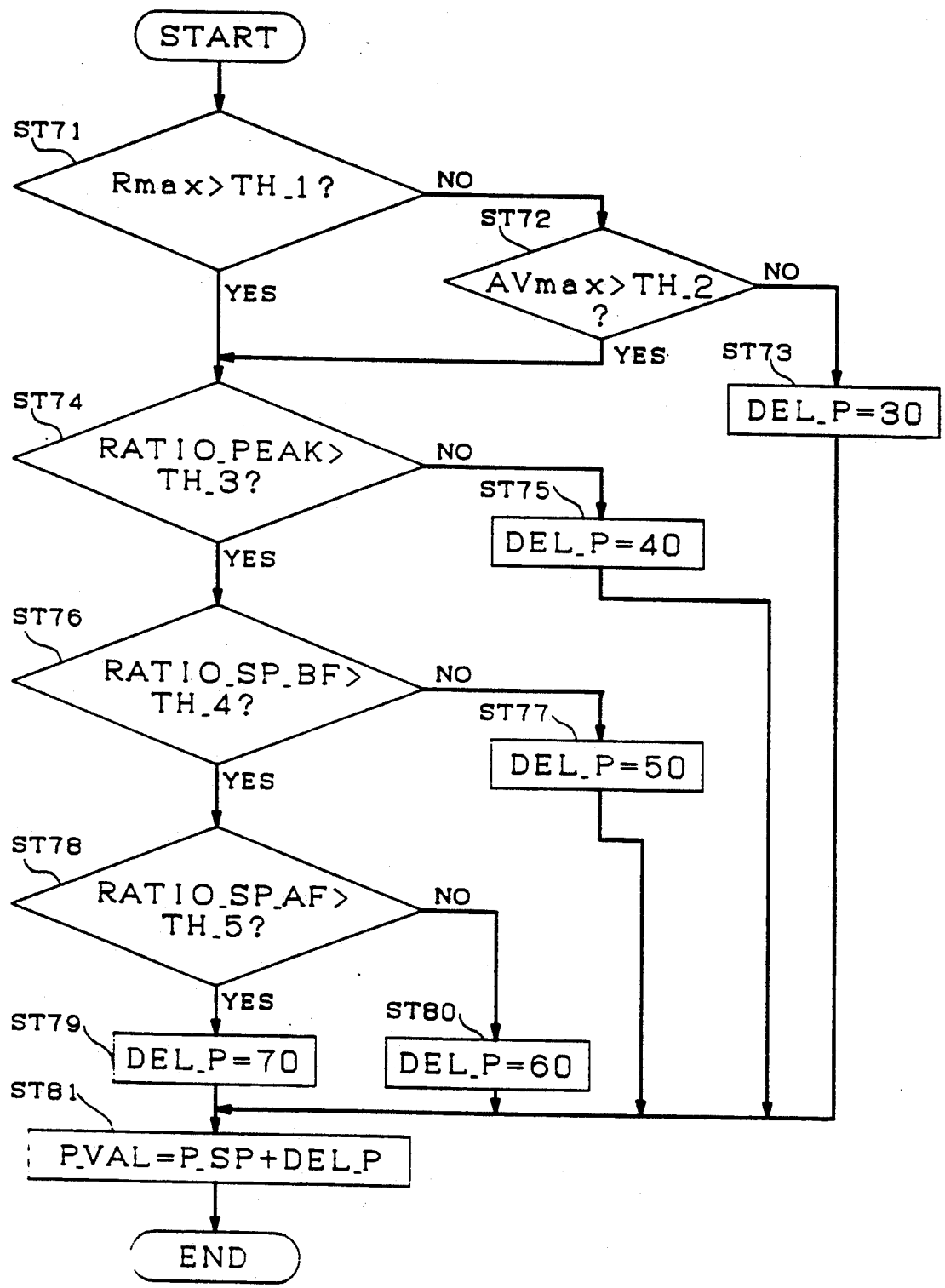
FIG. 20 is a flow chart illustrating a pressurization volume setting routine in the electronic blood pressure meter.

FIG. 20 shows a detailed flow chart for setting pressurization volume by the characteristic quantity in ST8. In the following explanation, TH_2 is a threshold value of an average value of pulse wave amplitudes, TH_3 is a threshold value of a ratio of inclination of amplitudes before and after the maximum point, TH_4 is a threshold value of a ratio of pressure, and TH_5 is a threshold value of a ratio of inclination of pulse wave amplitude just after systolic pressure.

Upon entering the pressurization volume setting routine, it is inquired if a ratio Rmax of inclination of the maximum pulse wave amplitude is larger than TH_1 (ST71). Unless larger, it is inquired if the average AVmax of pulse wave amplitudes is larger than the threshold value TH_2 (ST72). Unless larger in ST72, the pulse wave is judged as a normal wave and the margin volume DEL_P is set to 30 (ST73). If a YES response is obtained in either ST71 or ST72, it is inquired if a ratio RATIO_PEAK of inclination of amplitudes before and after the maximum point is larger than the threshold value TH_3 (ST74). Unless larger, the margin volume DEL_P is set to 40 (ST75).

If a YES response is generated from ST74, it is inquired if the inclination of pulse wave amplitude RATIO_SP_BF just before systolic pressure is larger than the threshold value TH_4 (ST76). Unless larger, the margin volume DEL_P is set to 50 (ST77). If a YES response is generated from ST76, it is inquired if ratio of pulse wave amplitude just after systolic pressure RATIO_SP_AF is larger than the threshold value TH_5 (ST78). Unless larger, the margin volume DEL_P is set to 60 (ST80). If the ratio is larger the value, it is determined that the unusual degree of pulse wave component is greatly high and margin volume DEL_P is set to 70 (ST79). Thus, if the margin volume DEL_P is set, the margin volume is added to the systolic pressure estimated value P_SP to compute a pressurization volume P_VAL (ST81).

According to this invention, dispersion of pulse wave component is detected in an increasing process and a pressurization volume is controlled in accordance with the dispersion degree, so that in an irregular pulse patient precise blood pressure measurement can be performed without redepressurization and remeasuring by setting a large pressurization. In case of a person who rarely has an irregular pulse, measuring time can be decreased without decreasing measurement accuracy by setting a necessary minimum pressurization margin.

It should be understood that the above description is merely illustrative of this invention and that many changes and modifications may be made by those skilled in the art without departing from the scope of the appended claims.

What is claimed is:

1. An electronic blood pressure meter comprising:

a cuff;

pressurizing means for inflating the cuff;

pressure sensing means for sensing a fluid pressure within the cuff;

pulse wave detecting means for detecting a pulse wave component included in the cuff;

systolic pressure estimating means for estimating a systolic pressure value based on the pulse wave and the cuff pressure detected during inflation by the pressurizing means;

pressurization volume computing means for computing a pressurization volume based on the estimated systolic pressure value;

pressure decreasing means for decreasing the cuff pressure after reaching the pressurization volume;

blood vessel information detecting means for detecting blood vessel information in the pressure decreasing process;

blood pressure value determining means for determining systolic and diastolic pressure values based on the blood vessel information and the cuff pressure;

pulse wave component dispersion degree detecting means for detecting a dispersion degree of the pulse wave components obtained in the pressure decreasing process; and pressurization volume controlling means for controlling the pressurization volume by said pressurizing means.

2. An electronic blood pressure meter comprising:

a cuff;

pressurizing means for inflating the cuff;

pressure sensing means for sensing a fluid pressure within the cuff;

pulse wave detecting means for detecting a pulse wave component included in the cuff;

systolic pressure estimating means for estimating a systolic pressure value based on the pulse wave and the cuff pressure detected during inflation by the pressurizing means;

pressurization volume computing means for computing a pressurization volume based on the estimated systolic pressure value;

pressure decreasing means for decreasing the cuff pressure after reaching the pressurization volume;

blood vessel information detecting means for detecting blood vessel information in the pressure decreasing process;

blood pressure value determining means for determining systolic and diastolic pressure values based on the blood vessel information and the cuff pressure;

pulse period computing means for computing a pulse period of said pulse wave component detected in the pressurizing process;

dispersion computing means for computing dispersion of the pulse period based on the computed several pulse period data; and pressurization volume controlling means for controlling a pressurization volume by said pressurizing means in accordance with the dispersion of the computed pulse period.

3. An electronic blood pressure meter comprising:

a cuff;

pressurizing means for inflating the cuff;

pressure sensing means for sensing a fluid pressure within the cuff;

pulse wave detecting means for detecting a pulse wave component included in the cuff;

systolic pressure estimating means for estimating a systolic pressure value based on the pulse wave and the cuff pressure detected during inflation by the pressurizing means;

pressurization volume computing means for computing a pressurization volume based on the estimated systolic pressure value;

pressure decreasing means for decreasing the cuff pressure after reaching the pressurization volume;

blood vessel information detecting means for detecting blood vessel information in the pressure decreasing process;

blood pressure value determining means for determining systolic and diastolic pressure values based on the blood vessel information and the cuff pressure;

dispersion degree computing means for computing a dispersion degree of the pulse wave amplitude based on several pulse data about said pulse wave amplitude computed in the pressurizing process; and pressurization volume controlling means for controlling a pressurization volume by said pressurizing means in accordance with the dispersion of the computed pulse period.

* * * * *